United States Patent [19]

Mach

[11] Patent Number: 5,074,005
[45] Date of Patent: Dec. 24, 1991

[54] FLOSS BUNDLE TOOTHBRUSH WITH OPTIONAL REPLACEABLE TOOTHPICK FEATURE

[76] Inventor: Stanley Mach, 1201 NW. 87th Way, Pembroke Pines, Fla. 33024

[21] Appl. No.: 524,902

[22] Filed: May 18, 1990

[51] Int. Cl.$^5$ ............................................. A47C 25/00
[52] U.S. Cl. .................... 15/105; 15/167.1; 15/177; 15/210 R; 128/62 A; 132/309; 132/321
[58] Field of Search ............... 15/105, 167.1, 167.2, 15/176.3, 176.6, 177, 210 R, 229.1; 132/309, 321, 326, 327; 433/147; 128/62 A; 24/514, 525, 569

[56] References Cited

U.S. PATENT DOCUMENTS

| | | | |
|---|---|---|---|
| 624,211 | 5/1899 | Hill | 24/525 |
| 781,292 | 1/1905 | Murphree | 15/177 |
| 1,289,325 | 12/1918 | Wake | 15/210 R |
| 1,492,360 | 4/1924 | Davis | 15/210 R |
| 1,559,519 | 10/1925 | Buckley | 15/210 R |
| 1,635,924 | 7/1927 | Buckley | 15/210 R |
| 1,646,082 | 10/1927 | Dailey | 132/309 |
| 2,146,290 | 2/1939 | Doyle | 15/210 R |
| 3,469,810 | 9/1969 | Dorris | 24/525 |
| 3,892,040 | 7/1975 | Marquis | 132/321 |
| 4,280,518 | 7/1981 | Gambaro . | |
| 4,296,518 | 10/1981 | Furrier et al. | 15/110 |
| 4,564,035 | 1/1986 | Turner . | |
| 4,574,823 | 3/1986 | Uriss . | |
| 4,710,996 | 12/1987 | Tarrson et al. | 15/105 |
| 4,787,403 | 11/1988 | Chen . | |
| 4,790,336 | 12/1988 | Kuo . | |

FOREIGN PATENT DOCUMENTS

| | | | |
|---|---|---|---|
| 144980 | 10/1903 | Fed. Rep. of Germany | 15/210 R |
| 351365 | 2/1961 | Switzerland | 128/62 A |
| 3293 | 2/1916 | United Kingdom | 15/229.1 |

Primary Examiner—Timothy F. Simone
Assistant Examiner—Mark Spisich
Attorney, Agent, or Firm—Alvin S. Blum

[57] ABSTRACT

A toothbrush comprising a floss bundle primary cleaning element instead of conventional bristles. The floss bundle, having no sharp tips, can clean, absorb and polish without risk of cutting gums. No toothpaste is required. Because of the soft, smooth nature of the floss bundle, the invention can be used dry as well as wet, and, thus, function safely and properly where no water is available. This floss bundle is held in a clamp, having upper and lower jaws, fixed at one end of a handle. The lower jaw comprises a sleeve which encircles a threaded bolt formed at this end of the handle. The clamp jaws are opened and closed by rotating a nut located just below the lower jaw, also encircling the bolt. In this way the floss bundle can be removed and replaced between uses. The other end of the handle is also formed into a threaded bolt, having a hole diametrically bored through it, into which the wide end of a half toothpick is removably fitted. The toothpick is secured in place by rotating a nut encircling this bolt unit the nut advances into contract with the protruding toothpick, forming a friction grip. Once used, the toothpick is released by rotating the nut in the opposite direction, and then removed with the user's fingers.

15 Claims, 2 Drawing Sheets

FLOSS BUNDLE TOOTHBRUSH WITH OPTIONAL REPLACEABLE TOOTHPICK FEATURE

BACKGROUND OF THE INVENTION

1. Field of the Invention

The present invention relates generally to the field of dental care, and more particularly to a toothbrush having a replaceable floss bundle instead of bristles, to polish teeth and clean gums, and also having a replaceable toothpick.

2. Description of the Prior Art

Conventional toothbrushes are equipped with hard, resilient bristles, the tips of which slide across tooth surfaces to remove debris. These hard, sharp tips can cut soft gum tissue, particularly where no water is available to wet and lubricate bristles. Although some tooth polishing can be accomplished in conjunction with an abrasive toothpaste, bristle tips do not provide the broad surface contact necessary for achieving a good polish. Since these hard bristles have little or no absorption capacity, their ability to remove stains is also limited. Finally, the bristles are reused from one cleaning to the next, and bristles damp from one use become a fertile breeding ground for bacteria. Thus the conventional bristles can become unsanitary. The latter can also be said of the conventional rubber toothpicks permanently mounted at the base of the handle.

All of these conventional shortcomings are exemplified in U.S. Pat. No. 4,296,518. This patent, issued to Furrier, et al, in 1981, discloses essentially a typical toothbrush with bristles embedded in one end of a handle and a rubber toothpick permanently mounted at the other end.

As to inventions related to dental floss use, these generally have been confined to securing a single strand or segment of floss between two points to facilitate insertion of the floss between teeth. These devices are therefore, by their construction and purpose, restricted to cleaning interfacial tooth surfaces only. Examples of such common devices are: Kuo, U.S. Pat. No. 4,790,336, which discloses a floss storage spool and a strand segment holding fork; Chen, U.S. Pat. No. 4,787,403, which also discloses a strand segment holding fork, at the end of a handle and comprising a screw mechanism for securing the ends of the floss strand; Gambaro, U.S. Pat. No. 4,280,518, which teaches a C-shaped strand segment holding member, attached to one end of handle having several circumferential rows of cleaning bristles at the other end; and Uriss, U.S. Pat. No. 4,574,823, which discloses a C-shaped strand holder, handle, and enclosed floss spool which feeds the strand holder through a channel in the handle. Turner, U.S. Pat. No. 4,564,035, discloses a complicated toothpick holder and tubular handle, wherein the toothpick is secured in the adjustable hook apparatus.

OBJECTS OF THE INVENTION

It is the object of this invention to remedy the above, as well as related deficiencies in the prior art.

More specifically, it is the principle object of the present invention to provide a floss or string bundle cleaning element which can remove food particles from teeth and dead tissue from gum surfaces, and also polish teeth and absorb stains, and perform these functions either wet or dry, and without exposing soft gums to hard, sharp bristle points. It is another object of the present invention to provide a toothbrush with a cleaning element which can be replaced from one cleaning to the next, thereby substantially reducing unsanitary bacterial build-up on the damp cleaning element.

It is yet another object of the present invention to provide a toothpick holder which allows easy removal and replacement of the toothpick from one cleaning to the next and, thus, remains sanitary. It is yet another object of the present invention to provide a floss bundle and toothpick holding toothbrush simple to operate and of simple construction.

SUMMARY OF THE INVENTION

The above and related objects are achieved by providing a toothbrush with a floss bundle primary cleaning element in place of conventional bristles. The floss bundle, having no sharp tips, can clean, absorb and polish without risk of cutting gums. No toothpaste is required. Because of the soft, smooth nature of the floss bundle, the invention can be used dry as well as wet, and, thus, function safely and properly where no water is available.

This floss bundle is held in a clamp, having upper and lower jaws, fixed at one end of a handle. The lower jaw comprises a sleeve which encircles a threaded bolt formed at said end of the handle. The clamp jaws are opened and closed by rotating a nut located just below the lower jaw, also encircling the bolt. In this way the floss bundle can be removed and replaced between uses.

The other end of the handle is also formed into a threaded bolt, having a hole diametrically bored through it, into which the wide end of a half toothpick is removably fitted. The toothpick is secured in place by rotating a nut encircling this bolt until the nut advances into contact with the protruding toothpick, forming a friction grip. Once used, the toothpick is released by rotating the nut in the opposite direction, and then removed with the user's fingers.

The axis of the bolts may be angled a few degrees away from the axis of the central body of the handle to permit the floss bundle and toothpick cleaning elements to reach remote areas in the user's mouth. Corners of the handle, clamp and bolts are rounded to prevent discomfort from contact with soft mouth tissue during use.

DETAILED DESCRIPTION OF THE INVENTION INCLUDING THE PREFERRED EMBODIMENT

Figure 1:
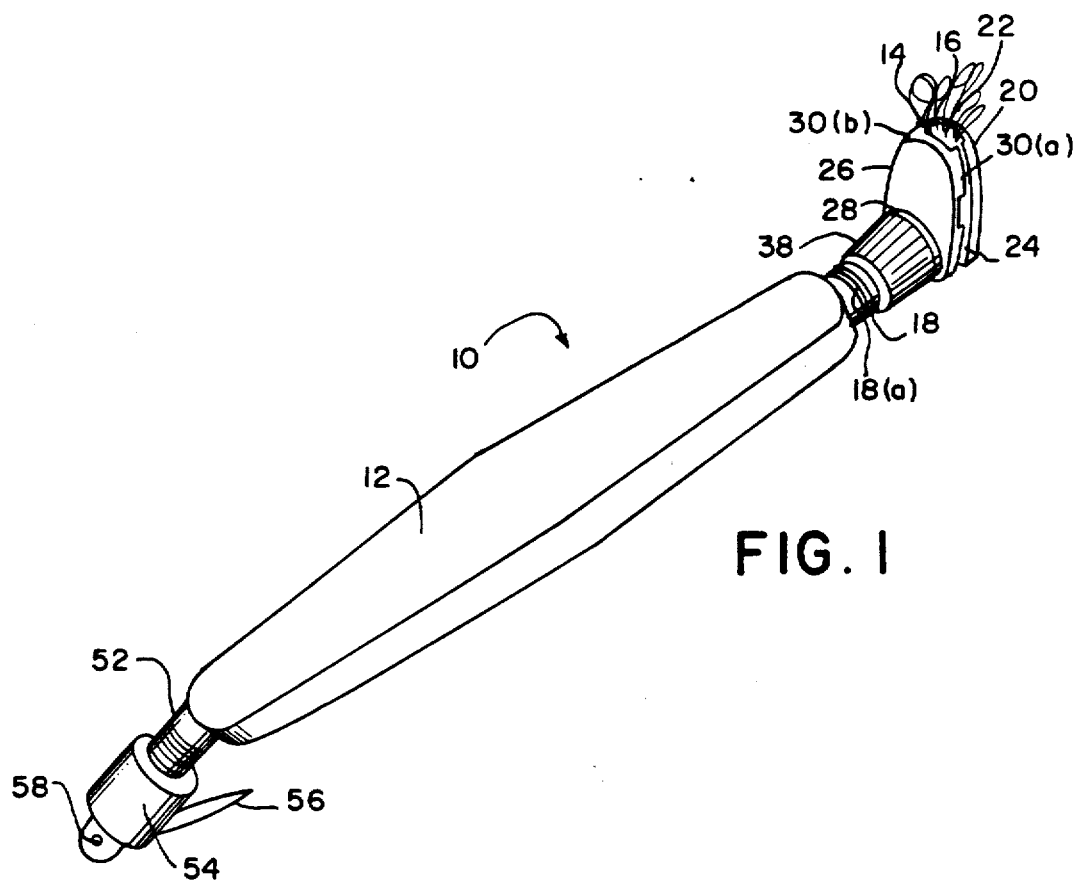
FIG. 1. is a perspective view illustrating the present invention, showing the clamp partially open and showing a half toothpick in the securing passageway.
Figure 3:
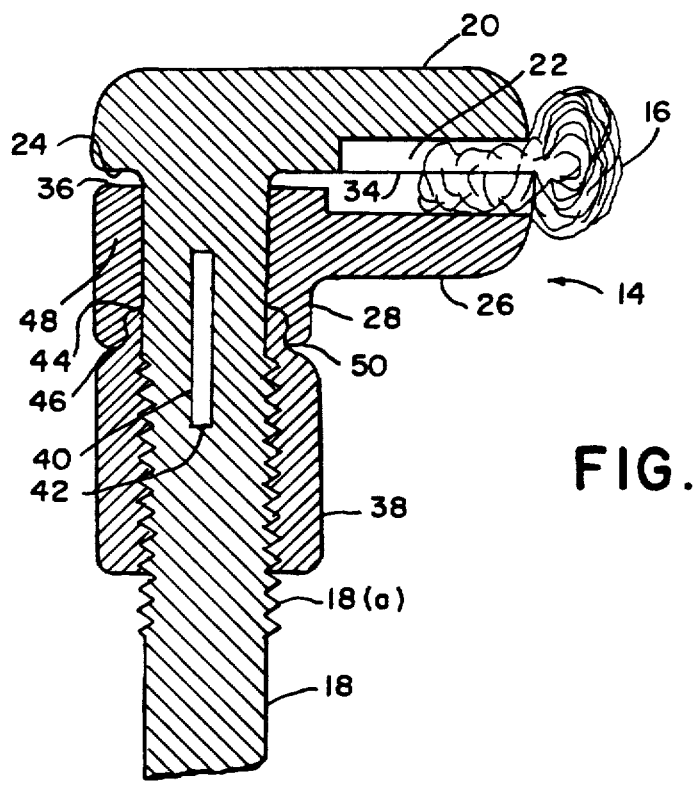
FIG. 3. is a cross-sectional side view of the floss bundle clamp portion of the invention, with a floss bundle secured in the clamp.
Figure 4:
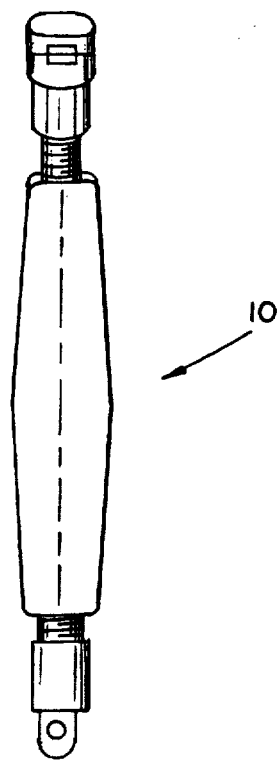
FIG. 4. is a side-view of the invention, showing the angled position of the bolts relative to the central body of the handle.

Referring now to the drawings, and more particularly to FIG. 1 and FIG. 3, the present invention is directed to a floss bundle toothbrush and replaceable toothpick denoted generally by reference numeral (10). For the purposes of this invention, a floss or string bundle comprises one or more segments of floss or string wound either around itself or another object to present a surface area broader than that of a single strand of floss or string. In its preferred embodiment, this bundle is roughly spherical and approximately one-quarter inch (¼") in diameter. The toothbrush (10) comprises a flat plastic handle (12) having a broad midsection and tapering toward the ends to aid the user in grasping and holding the invention. The preferred length of the handle (12) is approximately that of a conventional toothbrush handle. The upper end of the toothbrush (10) comprises a clamp (14), extending perpendicularly out from the axis of the handle (12), for gripping part of a small bundle of floss (16). The floss bundle (16) is gripped by the clamp (14) so that part of the bundle (16) protrudes beyond the end of the clamp (14). This protruding part of the bundle (16) serves as the primary cleaning element of the invention and is rubbed against the user's teeth and gums to clean and polish. The clamp (14) outer edges are rounded to minimize discomfort during use.

Figure 2:
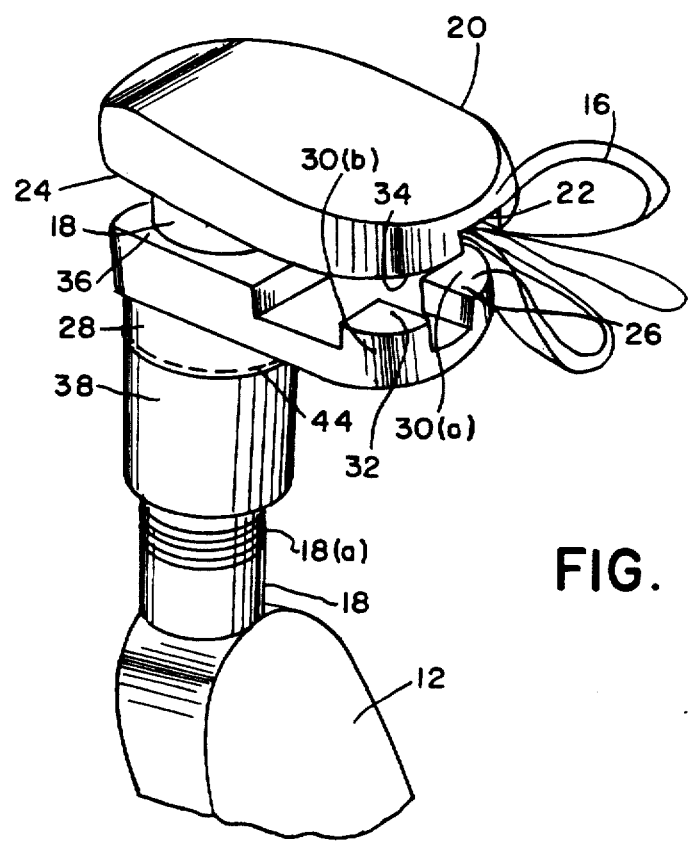
FIG. 2. is an enlarged, perspective view of the floss bundle clamp portion of the invention, showing the clamp partially open.

FIG. 2 is an enlarged, perspective view of the clamp (14) portion of the invention. The upper end of the handle (12) is formed into a cylindrical shaft or bolt (18) having a threaded section 18(a) and terminating in a perpendicular upper jaw 20 approximately one-half inch (½") in length and one-quarter inch (¼") in width. A rectangular channel (22) having a width approximately one third that of the clamp (14) and a depth approximately half again its width is recessed axially into the lower surface of the upper jaw (20). The purpose of this channel (22) is to receive part of the floss bundle (16) and help hold it securely when the clamp (14) is closed. The upper jaw (20) extends perpendicularly out from the jaw bolt (18) forming an upper jaw rim (24) circumferentially about the bolt (18).

The lower jaw (26) comprises a sleeve (28) which encircles the jaw bolt (18) in sliding contact therewith, and a gripping portion extending out perpendicular to the bolt (18) axis in the same direction as the upper jaw. Said sleeve (28) has an upper rim (36). The lower jaw (26) has the same length and width as the upper jaw (20). Two flat-topped teeth (30)(a) and (b) are formed on the upper surface of the lower jaw (26), at the remote edge thereof from the handle (12), symmetrically about the longitudinal axis of the clamp (14). The upper surfaces (32) of these teeth (30) correspond in width and position with the channel (22) lower side surfaces (34) of the upper jaw (20). The upper surfaces (32) of the flat-topped teeth (30) and the sleeve (28) upper rim (36) are in the same plane, perpendicular to the axis of the handle (12), so that the sleeve (28) upper rim (36) contacts the upper jaw rim (24) simultaneously with the tooth upper surfaces (32) making contact with the channel (22) side surfaces. The lower jaw (26) is slid up and down the jaw bolt (18) to open and close the clamp (14), by means of a jaw adjusting nut (38) adjacent to its sleeve (28). This nut (38) is internally threaded and encircles the jaw carriage bolt (18) just below the jaw sleeve (28). The segment of the jaw bolt (18) encircled by the jaw nut (38) is threaded over a length equivalent to that of the nut (38) plus about one-quarter inch (¼"). The bolt threads extend up toward the clamp (14) just far enough to permit the nut (38) to rotate and advance up the bolt until it pushes the lower jaw (26) into contact with the upper jaw (20). When the nut (38) is rotated to its lowest position, the clamp (14) opens to create a gap between the jaws (26) and (20) of about one-quarter inch (¼"). This gap is sufficient to permit insertion of a floss bundle (16) into the clamp (14).

The lower jaw (26) is restrained from rotation relative to the upper jaw (20) by means of a key (40). This is shown is FIG. 3, which is a cross-sectional side view of the clamp portion of the invention. This key (40) is fitted into a keyway (42) cut into the bolt (18) outer surface and into the corresponding sleeve 28 inner surface. Said key (40) and keyway (42) are positioned and of sufficient length to prevent the sleeve (28) from rotating about the jaw bolt (18) throughout the sleeve's entire range of movement along the bolt (18).

The outer surface of the nut (38) is cylindrical and knurled to permit easy grasping and turning with the users' fingers. The jaw nut (38) has a circumferential ridge (44) formed at its upper edge (46) which snaps into a corresponding circumferential recess (48) in the lower rim (50) of the jaw sleeve (28). This permanent interlock between the sleeve (28) and the nut (38) prevents the lower jaw (26) from moving up or down the bolt (18) independently of the nut (38), so that the clamp (14) is always opened or closed by rotating the nut (38).

The user rotates the jaw nut (38) one way to open the clamp (14), places part of the floss bundle (16) between the jaws (20) and (26), and then secures said bundle (16) in the clamp (14) by rotating the jaw nut (38) in the other direction, thus closing the jaws around part of the bundle (16). The bundle (16) is held securely in the clamp (14) by the lower jaw teeth (30) (a) and (b) which become embedded in the bundle (16) and the upper jaw (20) channel (22) which contains some of the bundle (16).

The toothpick end of the handle (12) which is the lower end of the handle (12), is formed into threaded bolt (52), similar to jaw bolt (18), and encircled by a similar knurled nut (54). The lower end of the bolt (52) is also the lower end of the handle (12). Bolt (52) contains a diametrically directed hole, said hole having a constant diameter of about ⅛th inch and the axis of which is parallel to the axis of the clamp (14) at the other end of the handle. A broken off half of an ordinary wooden toothpick (56) is fitted into this hole, termed the toothpick receiving passageway (58). This toothpick (56) is positioned in the passageway (58) so that the broken end is contained within the passageway (58) and the point protrudes from the handle (12). The toothpick (56) is secured in the passageway (58) by rotating the toothpick securing nut (54) so that the nut (54) makes tight contact with the toothpick (56), thus binding the toothpick (56) in place with a friction fit. Once used, the toothpick (56) can be released by rotating the securing nut (54) in the other direction. The user then lifts the toothpick (56) out of the passageway (58) and replaces it with a fresh toothpick, in the manner described above. This replaceable toothpick feature permits the user to supplement the floss bundle (16) cleaning and polishing with cleaning between the user's teeth and closely along the edge of the gums, and to do so with a fresh toothpick for each cleaning.

Figure 5:
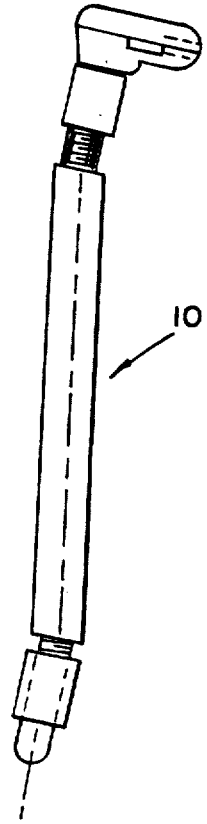
FIG. 5. is a front-view of the invention, showing the broad-mid-section contour of the handle.

The axis of the two bolts, (18) and (52), may be offset a few degrees from the axis of the central body of the handle so that the two cleaning elements, the floss bundle and toothpick, can more easily reach remote area of the user's mouth. This offset would ordinarily be between ten (10) and thirty (30) degrees. See FIG. 5 for illustration.

The entire construction of this floss bundle toothbrush is such that no metal parts need be used. The entire toothbrush assembly, bolts and nuts can be manufactured from many different plastics, preferably of medical grade.

While the invention has been described, disclosed, illustrated and shown in certain terms or certain embodiments or modifications which it has assumed in practice, the scope of the invention is not intended to be, nor should it be, deemed to be limited thereby and such other modifications or embodiments as may be suggested by the teachings herein are particularly reserved, especially as they fall within the breadth and scope of the claims here appended.

What is claimed:

1. A dental cleaning device comprising:
   an elongate handle having a first end, a second end and a longitudinal axis;
   clamp means connected to said first end for removably clamping a tooth cleaning element, said element comprised of flaccid filamentous material coiled upon itself into a bundle; said clamp means having a closeable elongate channel with one open short end and one closed short end extending along a radius of said axis; said channel receiving a first portion of said bundle, whereby a second portion of said bundle protrudes radially from said open short end to provide a plurality of soft loops for tooth cleaning directed radially from said axis of said handle.

2. The device according to claim 1, in which said flaccid material is string.

3. The device according to claim 1, in which said flaccid material is dental floss.

4. The device according to claim 1, in which said clamp means comprises:
   a threaded bolt member affixed at one end to said first end of said handle, and at another end to a stationary jaw element;
   a movable jaw element slideably arranged on said bolt member for axial movement thereon, said stationary and movable jaw elements defining said channel; and
   a threaded sleeve means threadably engaged upon said bolt member and cooperating with said moveable jaw element whereby rotation of said sleeve means in a first direction closes said channel and rotation in a second direction opens said channel.

5. The device according to claim 4, in which said flaccid material is string.

6. The device according to claim 4, in which said flaccid material is a single length of string.

7. The device according to claim 4, in which said flaccid material is dental floss.

8. The device according to claim 4, in which said flaccid material is a single length of dental floss.

9. The device according to claim 4 further comprising toothpick holding means for removeably holding a toothpick substantially transverse to said longitudinal axis, said toothpick holding means connected to said second end of said handle.

10. The device according to claim 9, in which said toothpick holding means comprises:
    a bolt element extending substantially along said longitudinal axis and having a toothpick receiving aperture extending transversely therethrough;
    a threaded sleeve means threadably engaged upon said bolt element for advancing and retreating upon said bolt element by rotation thereon;
    whereby rotation of said sleeve means in a first direction forces said sleeve means against a side of said toothpick and thereby secures a toothpick received in said aperture, and rotation in a second direction releases a toothpick received in said aperture.

11. The device according to claim 1 further comprising toothpick holding means for removably holding a toothpick substantially transverse to said longitudinal axis, said toothpick holding means connected to said second end of said handle.

12. The device according to claim 11, in which said toothpick holding means comprises:
    a bolt element extending substantially along said longitudinal axis and having a toothpick receiving aperture extending transversely therethrough;
    a threaded sleeve means threadably engaged upon said bolt element for advancing and retreating upon said bolt element by rotation thereon;
    whereby rotation of said sleeve means in a first direction forces said sleeve means against a side of said toothpick and thereby secures a toothpick received in said aperture, and rotation in a second direction releases a toothpick received in said aperture.

13. A dental cleaning instrument, comprising:
    an elongate handle having a longitudinal axis, a hand-gripping portion, a first end and a second end;
    a stationary clamping member fixed to said first end;
    a moveable clamping member slideably mounted for axial motion on said first end between said stationary member and said hand-gripping portion;
    a locking member engaged upon said first end between said moveable member and said hand-gripping portion, said locking member operatively connected to said moveable member whereby movement of said locking member in a first direction advances said moveable member toward said stationary member and movement of said locking member in a second direction moves said clamping member away from said stationary member, said stationary and moveable members defining the two long sides of a clamping channel, said channel being a narrow elongate channel extending substantially along a radius transverse to said longitudinal axis from said first end which defines a closed end of said channel to an open end facing away from said first end;
    a soft tooth cleaning element comprised of a flaccid filamentous material coiled upon itself to form a bundle;
    wherein said clamping channel is arranged to removeably clamp and enclose a first portion of said cleaning element, whereby a second portion of said cleaning element extends radially from said open end of said channel to provide a plurality of soft cleaning loops projecting laterally from said longitudinal axis for enhanced positioning within the mouth.

14. The instrument according to claim 13, further comprising a toothpick holding means for removeably clamping a toothpick connected to said second end, said toothpick holding means including:
    a toothpick-receiving aperture extending through said second end substantially transversely to said longitudinal axis;

a sleeve element threadably engaged upon said second end between said aperture and said hand-gripping portion, said sleeve element arranged to engage a toothpick laterally when received within said aperture for removeably securing a toothpick thereby.

15. The instrument according to claim 13, in which said locking member is threadably engaged upon said first end.

* * * * *